United States Patent

Matsumoto et al.

Patent Number: 5,888,823
Date of Patent: Mar. 30, 1999

[54] STANDARD FLUID FOR FLOW CYTOMETER

[75] Inventors: Teruya Matsumoto, Hyogo-ken; Masakazu Fukuda, Kobe, both of Japan

[73] Assignee: Toa Medical Electronics Co., Ltd., Kobe, Japan

[21] Appl. No.: 747,644

[22] Filed: Nov. 13, 1996

[30] Foreign Application Priority Data

Nov. 17, 1995 [JP] Japan .................................. 7-299845
Nov. 8, 1996 [JP] Japan .................................. 8-296654

[51] Int. Cl.⁶ .................................................. G01N 31/00
[52] U.S. Cl. .................................. 436/10; 436/8; 436/63; 436/164; 436/172
[58] Field of Search .................................. 436/8, 10, 16, 436/63, 164, 166, 172; 252/408.1

[56] References Cited

U.S. PATENT DOCUMENTS

| | | | |
|---|---|---|---|
| 4,704,891 | 11/1987 | Recktenwald et al. | 250/252.1 |
| 4,714,682 | 12/1987 | Schwartz | 436/10 |
| 4,734,403 | 3/1988 | Dussourd D'Hinterland et al. | 514/54 |
| 4,767,206 | 8/1988 | Schwartz | 436/10 X |
| 4,857,451 | 8/1989 | Schwartz | 436/10 X |
| 4,868,126 | 9/1989 | Schwartz | 436/10 |
| 5,073,497 | 12/1991 | Schwartz | 436/10 X |
| 5,073,498 | 12/1991 | Schwartz et al. | 436/10 X |
| 5,084,394 | 1/1992 | Vogt et al. | 436/10 X |
| 5,093,234 | 3/1992 | Schwartz | 436/10 X |
| 5,123,738 | 6/1992 | Yonemura | 356/243.2 |
| 5,380,663 | 1/1995 | Schwartz et al. | 436/10 |
| 5,456,102 | 10/1995 | Moorehead | 73/1.24 |
| 5,520,952 | 5/1996 | Tanitsu et al. | 427/58 |
| 5,620,842 | 4/1997 | Davis et al. | 436/10 X |
| 5,728,582 | 3/1998 | Taki et al. | 436/10 |

FOREIGN PATENT DOCUMENTS

| | | |
|---|---|---|
| 0 482 571 | 4/1992 | European Pat. Off. . |
| HEI.1-301166 | 12/1989 | Japan . |
| HEI.4-278460 | 10/1992 | Japan . |
| HEI.5-18061 | 3/1993 | Japan . |
| HEI.6-102152 | 4/1994 | Japan . |

*Primary Examiner*—Maureen M. Wallenhorst
*Attorney, Agent, or Firm*—Pearne, Gordon, McCoy & Granger LLP

[57] ABSTRACT

A standard fluid for a flow cytometer which shows, after staining, almost the same fluorescence intensity and scattered light intensity as those of the cells to be assayed.

5 Claims, 4 Drawing Sheets

ര,888,823

STANDARD FLUID FOR FLOW CYTOMETER

TECHNICAL FIELD

This invention relates to a standard fluid to be used in the quality control and calibration of a flow cytometer. More particularly, it relates to a standard fluid for a flow cytometer for analyzing cells contained in urine.

BACKGROUND ART

There has been known to use a flow cytometer for classifying and counting cells in blood or particles in urine. This method comprises staining cells in a sample with a staining solution, passing the stained cells one by one through a flow cell under irradiating with excitation light beams and measuring the fluorescence or scattered light generated from the cells to thereby classify and count the cells.

In the analysis with the use of a flow cytometer, it is necessary to calibrate the device so as to obtain precise data. It has been a practice to use fixed cells (for example, red blood cells, bacteria), latex particles or fluorescent particles for the quality control and calibration of a flow cytometer. For example, Japanese Laid-Open Patent Publication No. 6-102152 has disclosed a standard fluid for a flow-type particle image analyzer with the use of an ion exchange resin, while Japanese Laid-Open Patent Publication No. 4-278460 has proposed to use cells, bacteria, latex particles, microcapsules, starch grains, gelatin grains and pollens as marker particles.

However, materials with biological origins such as cells and bacteria show large differences among individuals, which makes it difficult to establish stable qualities. In addition, troublesome procedures (for example, preventive measures against the infection with pathogenic organisms, cold storage) are required in handling these materials.

On the other hand, latex particles cannot be stained in general and, therefore, are not usable in a system of controlling a staining solution. Fluorescent particles bonded to a fluorescent dye are usable in an optical control system but not in a system of controlling staining wherein not only the staining solution per se but also the staining conditions (the amount of the staining solution to be pipetted, temperature, etc.) should be managed. Further, microcapsules, starch grains, gelatin grains, etc. are sometimes different in staining modes from the cells to be assayed. This is seemingly because these particles differ from actual cells in the affinity for the dye contained in the staining solution. It is preferable that a calibration substance shows similar staining behaviors as those of the cells to be assayed, since the calibration and quality control can be facilitated thereby.

The standard fluid disclosed in Japanese Laid-Open Patent Publication No. 6-102152 as cited above is one to be used in a device for photographing and analyzing particles from the image of each particle. That is, this patent discloses no standard fluid to be used in a device for analyzing scattered light intensity or fluorescence intensity.

DISCLOSURE OF THE INVENTION

The present invention aims at providing a standard fluid for a flow cytometer which is free from the above-mentioned disadvantages encountering in the prior art, shows almost the same behaviors as those of the cells to be assayed and can be easily handled without any risk of infection.

To achieve the above-mentioned object, the present inventors have conducted extensive studies and, consequently, succeeded in the development of a standard fluid which contains no material with biological origin, can be stained with a staining solution and shows the same behaviors as those of the subject to be assayed.

Accordingly, the present invention provides a standard fluid for a flow cytometer characterized by containing particles which show, after staining, almost the same fluorescence intensity and scattered light intensity as those of the cells to be assayed.

BEST MODE FOR CARRYING OUT THE INVENTION

Figure 1:
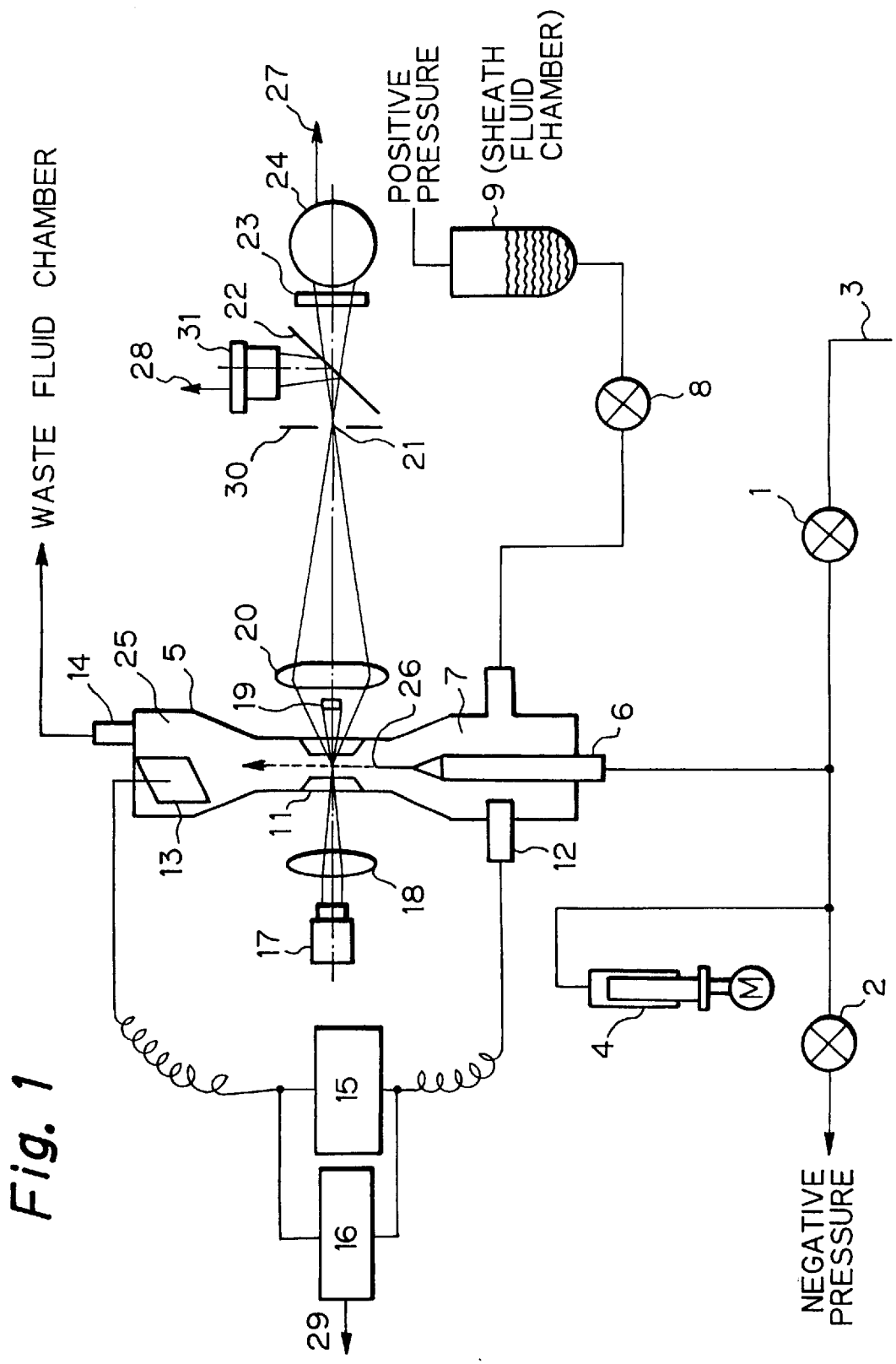
FIG. 1 is a schematic diagram of a flow cytometer.

The sample to be analyzed by using the standard fluid of the present invention are body fluids such as blood and urine containing red blood cells, white blood cells, platelets, etc. (in the case of blood) or red blood cells, white blood cells, epithelial cells, urinary casts, etc. (in the case of urine). Further, some urine samples contain microorganisms such as bacteria, fungi, protozoans and parasites due to topical or systemic infection. In the case of renal insufficiency, furthermore, urine samples contain chemical components and crystals composed of drugs and free fats. These components are the cells to be assayed in the present invention.

The standard fluid of the present invention contains particles which show, after staining, almost the same fluorescence and scattered light intensities as those of the cells to be assayed. As the particles to be used in the standard fluid of the present invention, therefore, selection should be made of those capable of adsorbing a dye in such an amount as to give almost the same fluorescence intensity as that of the cells to be assayed. Also, use can be made of particles as large as the cells to be assayed. However, the size of the particles to be used in the present invention is not always the same as that of the cells to be assayed, since the scattered light intensity is affected not only by the particle size but also by the surface conditions of the particles.

It is advantageous to further add a fluorescence sensitivity stabilizer to the standard fluid of the present invention, since changes in the stained mode of the particles during storage (i.e., changes in the fluorescence sensitivity) can be prevented thereby for a long time. Although the stained particles in the standard fluid of the present invention can sustain the stable state at room temperature for about three months even though the standard fluid contains no fluorescence sensitivity stabilizer, the addition of the fluorescence sensitivity stabilizer can further prolong the shelf life of the standard fluid (for examples eight months or longer at room temperature).

As the fluorescence sensitivity stabilizer, water soluble organic solvents are suitable and alcohols and glycols may be appropriately employed therefor. More particularly speaking, methanol, ethanol, propanol, isopropanol, ethylene glycol, diethylene glycol, etc. are usable therefor and ethanol is the most desirable one. Such a fluorescence sensitivity stabilizer may be used preferably at a concentration of 5 to 15 w/w %, still preferably 6 to 14 w/w %. The addition of such a component also contributes to the inhibition of the growth of saprophytic bacteria.

It is preferable to use spherical silica particles, still preferably particles of silica for liquid crystals spacers, in the standard fluid of the present invention. Also, particles usable as packing materials in liquid chromatography, in particular, crosslinked agarose particles and porous silica particles may be preferably employed in the standard fluid of the present invention.

Next, preferable particles for each cell component will be described in detail regarding the cells contained in urine by way of example.

Red blood cell

It is appropriate to use spherical silica particles of a high purity with a particle size of 3 to 15 $\mu$m, still preferably 5 to 10 $\mu$m. It is particularly preferable to use those employed in electronic materials such as liquid crystal spacers. For example, use can be made of HIPRESICA SP™ (average particle size: 5.1 $\mu$m) manufactured by Ube-Nitto Kasei Co., Ltd.

White blood cell

It is appropriate to use totally porous silica with a particle size of 5 to 20 $\mu$m (still preferably 7 to 15 $\mu$m) and a pore size of 5 to 100 nm (still preferably 7 to 10 nm). For example, use can be made of Zorobax BP-SIL™ (particle size: 7 to 8 $\mu$m, pore size; 7 to 8 nm) which is manufactured by ROCKLAND TECHNOLOGIES Inc. and obtained from GL Science Co., Ltd.

Epithelial cell

It is appropriate to use porous silica with a particle size of 15 to 300 $\mu$m (still preferably 20 to 200 $\mu$m) and a pore size of 5 to 40 nm (still preferably 10 to 100 nm). For example, use can be made of NUCLEOPREP™ (average particle size: 30 $\mu$m) which is manufactured by MACHEREY-NAGEL. Also use can be made of a cellulose gel (for example, Cellulofine™ manufactured by Chisso Corporation), a hydrophilic vinyl polymer gel (for example, TOYOPEAL HW™ manufactured by TOSOH Co., Ltd.), etc.

Urinary cast

It is appropriate to use a crosslinked agarose gel with a particle size of 25 to 300 $\mu$m, still preferably 40 to 200 $\mu$m. For example, use can be made of Sepharose CL-2B™ (particle size: 60 to 200 $\mu$m) manufactured by Pharmacia Biotec Co., Ltd.

Bacterium

It is appropriate to use totally porous, spherical silica with a particle size of 0.7 to 5 $\mu$m, still preferably 1 to 3 $\mu$m. For example, use can be made of Pia Seed™ (average particle size: 2 $\mu$m) manufactured by Pia TEC Co., Ltd.

To assay white blood cells, epithelial cells, blood casts and bacteria, it is preferable to use spherical particles which are commonly employed as a packing material in liquid chromatography and those having no chemical modification are appropriate therefor. However, these materials are cited merely by way of example and the particles to be used in the standard fluid of the present invention are restricted neither in particle size nor in material, so long as they can achieve almost the same fluorescence and scattered light intensities after staining as those of the cells to be assayed.

The particles cited above are those usable in the analysis of the cell components contained in urine. To analyze a blood sample which contains platelets in addition to red blood cells and white blood cells, it is preferable to use particles suitable for the analysis of platelets, for example, totally porous, spherical silica having a particle size of 1 to 5 $\mu$m, still preferably 2 to 4 $\mu$m.

The standard fluid for a flow cytometer of the present invention can be prepared by suspending the particles in an aqueous medium which is a buffer preferably having a pH value of 3 to 7, still preferably 4 to 5. If necessary, physiological salts (for example, sodium chloride or potassium chloride), sugars (for example, glucose), albumin, hemoglobin, nitrites, preservatives, etc. may be further added thereto.

The standard fluid for a flow cytometer of the present invention can be prepared by suspending particles of a single type in an aqueous medium. Alternatively, it may be prepared by mixing two or more types of particles different from each other depending on the sample to be assayed.

Before using, the standard fluid for a flow cytometer of the present invention is mixed with a staining solution which has been prepared separately. The staining solution is prepared by dissolving one or more fluorescent dyes, selected depending on the cells to be assayed, in a solvent such as ethylene glycol, diethylene glycol or methanol. As the fluorescent dyes, it is preferable to use cationic dyes such as dicarbocyanine dyes (for example, 3,3'-dihexyl-2,2'-oxacarbocyanine iodide, 3,3'-dimethyl-2,2'-oxacarbocyanine iodide, 3,3'-dipropyl-2,2'-oxacarbocyanine iodide, 3,3'-dipentyl-2,2'-oxacarbocyanine iodide), Rhodamine dyes (for example, Rhodamine B, Rhodamine 6G) and dyes capable of specifically staining DNA (for example, ethidium bromide).

Quality control and calibration of a flow cytometer with the use of the standard fluid of the present invention may be performed by flowing a mixture of the flow cytometer standard fluid of the present invention with a staining solution through the flow cell of the flow cytometer. As the flow cytometer, it is possible to use, for example, a fully automated urine cell analyzer (Model UF-100, manufactured by TOA MEDICAL ELECTRONICS Co., Ltd.) for analyzing urine samples or automated reticulocyte analyzers (R-Series, manufactured by TOA MEDICAL ELECTRONICS Co., Ltd.) for analyzing blood samples.

Now, a method of the use of the standard fluid of the present invention will be illustrated by using a standard fluid for analyzing a urine sample. A mixture of the standard fluid with the staining solution (hereinafter referred to as the standard sample) is passed through the flow cell and irradiated with excitation light beams. Then the forward scattered light and fluorescence intensities from the formed components in the standard sample are measured. Thus, the formed components contained in the standard sample can be assayed. In assaying urinary casts, it is advantageous to measure the electric resistance signal intensity (i.e., volume information) of the standard sample too, thus elevating the detection sensitivity. To assay a urine sample, it is, therefore, preferable to employ a flow cytometer by which electric resistance signal and optical information can be measured. FIG. 1 shows a flow cytometer which may be preferably employed in the assay with the use of the standard fluid of the present invention.

Figure 7:
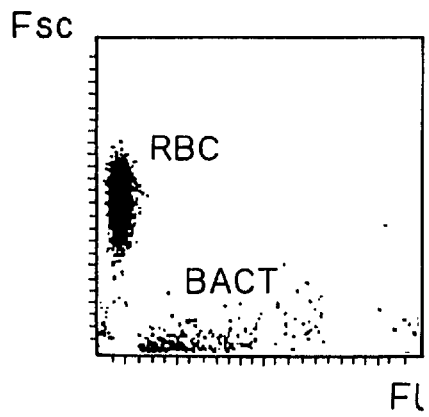
FIG. 7 is a two-dimensional scattergram of the forward scattered light intensity and the fluorescence intensity obtained by using a urine sample in which red blood cells and bacteria are observed.

First, valves 1 and 2 are opened for a definite period of time. Thus these valves 1 and 2 are filled up with the sample fluid supplied from a suction nozzle 3 due to the negative pressure from the waste chamber. As a syringe 4 presses out the fluid at a constant rate, the sample fluid is discharged from a sample nozzle 6. At the same time, a valve 8 is opened and thus a sheath fluid is supplied into a chamber 7 of a flow cell 5. Thus the sample is squeezed to fit to the inner diameter of the chamber 7 to thereby form a sheath flow, as shown in FIG. 7, which passes through an orifice 11. The orifice 11 is in the shape of a square tube of 100 to 300 $\mu$m in an inner side and made of an optical glass (including quartz glass). The formation of the sheath flow makes it possible to pass through the particles one by one in a line at the center of the orifice 11. The sample and sheath fluid passing through the orifice 11 are discharged via a recovery tube 14 connected to a chamber 25.

A platinum electrode 13 located in the chamber 25 serves as an anode, while a stainless electrode 12 located in the chamber 7 serves as a cathode. The electric resistance between these electrodes 12 and 13 is determined depending on the electrical resistivity (conductivity) of the sheath fluid, the pore size (pore cross section) and pore length of the orifice, the electrical resistivity of the sample fluid and the diameter of the sample flow.

An electrode 15 is a direct constant current source which supplies a constant current between the electrodes 12 and 13 so as to generate a current voltage depending on the electric resistivity and the current between the electrodes 12 and 13. When a particle passes through the orifice 11, the electric resistance varies at the both ends of the orifice 11. Namely, the electric resistance is elevated during the passage of the particle and thus the voltage between the electrodes 12 and 13 is varied. Further, there arises a pulse voltage in proportion to the size of the particle passing through the orifice 11. This voltage is added onto the current voltage as described above. The sum of these voltages thus observed between the electrodes 12 and 13 is detected with an amplifier 16 followed by the output of a resistance signal 29.

Light emitted from a laser 17 is converged by a condenser lens 18 and illuminates a sample flow 26 passing through the orifice 11 almost at the center. The laser light is in the form of an ellipse having the minor width (for example, about 10 $\mu$m) similar to the blood cell size in the direction of the sample flow and the major width (for example, about 150 to 300 $\mu$m) much broader than the blood cell particle in the direction perpendicular to the flow and light irradiation. In the laser light illuminating the sample flow 26, beams transmitted through the flow cell 5 as such without bumping against the cell (formed matter), i.e., the transmitted light are blocked by a beam stopper 19. On the other hand, the forward scattered light and forward fluorescence illuminating the cell (formed matter) and emitted at narrow angles are converged with a collector lens 20 and pass through a pinhole 21 of a blocking sheet 30. Next, these beams pass through a dichroic mirror 22. After the deletion of the scattered light with a filter 23, the fluorescence is detected with a photomultiplier tube (PMT) 24 and converted into an electric signal 27 followed by output. On the other hand, the dichroic mirror reflects the scattered light which is then received by a photodiode 31 and converted into another electric signal 28 followed by output.

When assay is carried out by the above-mentioned method with the use of the standard fluid for a flow cytometer of the present invention, the particles show almost the same behaviors as those of the cells to be assayed, which indicates that the standard fluid is usable in the calibration of the flow cytometer.

Function

When the standard fluid for a flow cytometer of the present invention is mixed with a staining solution, the dye is adsorbed onto the particles and emits fluorescence depending on the adsorption level.

The particles to be used in the standard fluid for a flow cytometer of the present invention are those capable of adsorbing a dye in such an amount as to achieve a fluorescence intensity similar to that of the cells to be assayed. Also, use can be made of particles as large as the cells to be assayed. However, the size of the particles to be used in the present invention may not always be the same as that of the cells to be assayed, since the scattered light intensity is affected not only by the particle size but also by the surface conditions of the particles.

For example, a cationic dye is used for staining cells. Compared with other cells, however, red blood cells have poor staining properties. Accordingly, it is preferable that the particles serving as a substitute for red blood cells would adsorb a dye not in a very large amount but to such an extent as to give a fluorescence intensity similar to that of the red blood cells, though particles adsorbing no dye cannot be employed therefor. The particles employed therefor have a size similar to the actual red blood cell size (3 to 10 $\mu$m). However, use can be also made of particles somewhat differing in size, so long as the scattered light intensity thereof is almost the same as that of the red blood cells.

On the other hand, particles serving as a substitute for white blood cells or epithelial cells, which are stained strongly, should adsorb a dye in such an amount as to achieve almost the same fluorescence intensity as those of these cells. The particles employed therefor have a size similar to the actual white blood cell size (3 to 15 $\mu$m) or epithelial cell size (15 to 150 $\mu$m), similar to the case of red blood cells. However, use can be also made of particles somewhat differing in size, so long as the scattered light intensity thereof is almost the same as that of the white blood cells or epithelial cells.

In the case of urinary casts, some contain inclusion bodies while others not. Thus particles serving as a substitute for blood casts of either type are used in the standard fluid of the present invention. Similar to other cells, the particles to be used therefor are those which adsorb a dye in such an amount as to achieve a fluorescence intensity similar to that of blood casts containing inclusion bodies and have a size similar to the actual blood cast size (100 µm or above), though particles somewhat differing in size are also usable therefor, so long as they can provide a scattered light intensity almost the same as that of the blood casts.

Similarly, the particles to be used as a substitute for bacteria (1 to 3 µm in size) are those which adsorb a dye in such an amount as to achieve a fluorescence intensity similar to that of bacteria and give a scattered light intensity similar to that of bacteria.

EFFECTS OF THE INVENTION

The present invention provides a standard fluid for a flow cytometer which shows almost the same behaviors as those of the cells to be assayed and can be easily handled without any risk of infection with bacteria, etc.

Further, the sensitivity of a flow cytometer can be precisely controlled by using particles of two or more types differing from each other in scattered light intensity and fluorescence intensity. For example, the total sensitivity is roughly regulated by using particles having a higher sensitivity followed by fine adjustment with the use of particles having a lower sensitivity.

To further illustrate the present invention in greater detail, the following Examples will be given. However, it is to be understood that the scope of the present invention is not restricted thereto.

EXAMPLE

Example 1

Assay of Standard Fluid for Urine Measurement

A standard fluid and a staining solution for urine examination of the following compositions were prepared.

| <Standard fluid> | |
| --- | --- |
| HIPRESICA SP™ (average particle size: 5.1 µm, for red blood cell, manufactured by Ube-Nitto Kasei Co., Ltd.) | 40/µl |
| Zorbax BP-SIL™ (particle size: 7–8 µm, for white blood cell, obtained from GL Science Co., Ltd.) | 40/µl |
| NUCLEOPREP 100-30™ (average particle size: 30 µm, for epithelial cell, manufactured by MACHEREY-NAGEL) | 40/µl |
| Sepharose CL-2B™ (particle size: 60 to 200 µm, for blood cast, manufactured by Phamacia Biotec Co., Ltd.) | 2/µl |
| Pia Seed S-150™ (average particle size: 2 µm) for bacteria, manufactured by Pia TEC Co., Ltd.) | 40/µl |
| sodium chloride | 10 g/l |
| sodium azide | 1 g/l |
| 50 mM citrate buffer solution, pH 4.0, conductivity: | 13 mS/cm. |

First, a thick dispersion containing exclusively the particles was prepared. After counting the particles under the conditions as specified below, the dispersion was diluted and blended so as to give the above-mentioned particle concentrations. Thus the standard fluid was obtained.

| <Staining solution> | |
| --- | --- |
| Staining reagent: | |
| 3,3'-dihexyl-2,2'-oxacarbocyanine | 0.144 w/w % |
| ethidium bromide | 0.036 w/w % |
| ethylene glycol | 99.820 w/w %. |
| Diluent for staining: | |
| HEPES | 1.165 w/w % |
| sodium hydroxide | 0.036 w/w % |
| EDTA-3K | 0.391 w/w % |
| purified water | suffice for 100%. |

The standard fluid, the staining reagent and the diluent for staining were mixed together at a ratio of 400:40:1160 (µl) and assay was performed at a reaction temperature of 35° C. for a staining period of 10 seconds with the use of UF-100 manufactured by TOA MEDICAL ELECTRONICS Co., Ltd.

Figure 2:
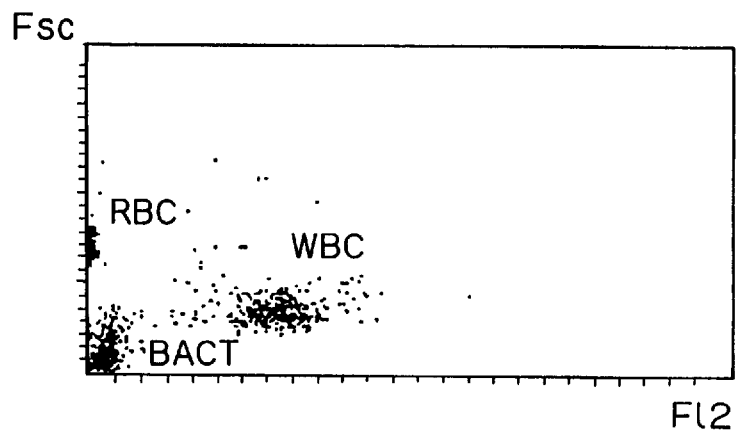
FIG. 2 is a two-dimensional scattergram of the forward scattered light intensity and the fluorescence intensity obtained by using the standard fluid of the present invention by which particles corresponding to red blood cells, white blood cells and bacteria can be separated and counted.

FIG. 2 is a two-dimensional scattergram of the forward scattered light intensity and the fluorescence intensity by which particles corresponding to red blood cells, white blood cells and bacteria can be separated and counted.

Figure 3:
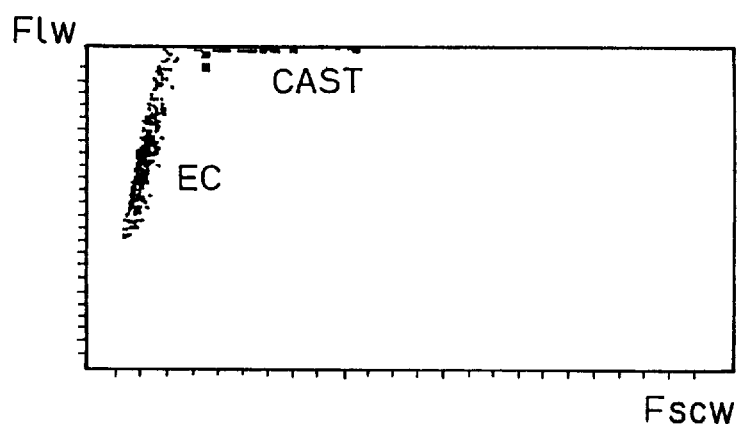
FIG. 3 is a two-dimensional scattergram of the fluorescence pulse width and the scattered light pulse width obtained by using the standard fluid of the present invention by which particles corresponding to epithelial cells and blood casts can be separated and counted.

FIG. 3 is a two-dimensional scattergram of the fluorescence pulse width and the scattered light pulse width by which particles corresponding to epithelial cells and large particles corresponding to blood casts (upper) can be separated and counted.

Figure 4:
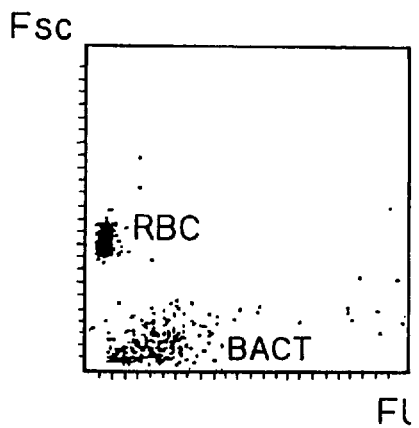
FIG. 4 is a two-dimensional scattergram of the forward scattered light intensity and the fluorescence intensity obtained by using the standard fluid of the present invention by which particles corresponding to red blood cells and bacteria can be separated and counted.

FIG. 4 is a two-dimensional scattergram of the forward scattered light intensity and the fluorescence intensity by which particles corresponding to red blood cells and bacteria can be separated and counted.

Figure 5:
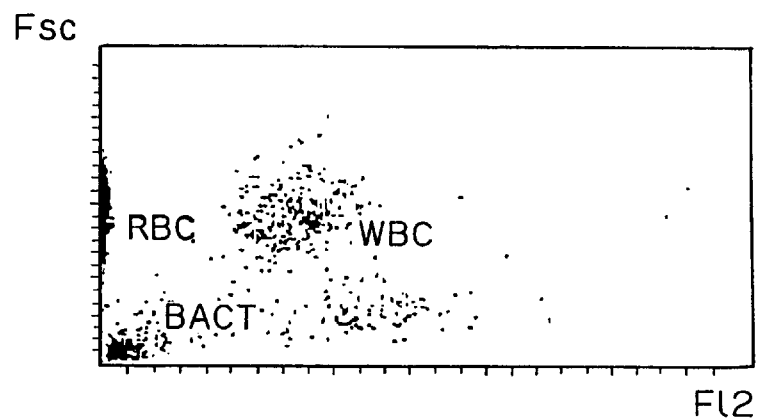
FIG. 5 is a two-dimensional scattergram of the forward scattered light intensity and the fluorescence intensity obtained by using a urine sample in which red blood cells, white blood cells and bacteria are observed.
Figure 6:
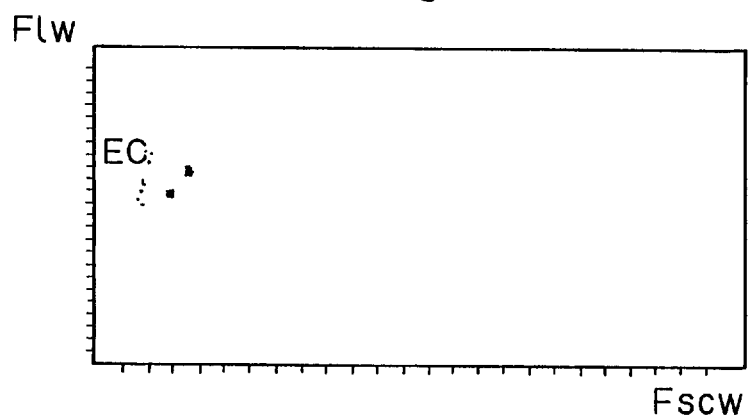
FIG. 6 is a two-dimensional scattergram of the fluorescence pulse width and the scattered light pulse width obtained by using a urine sample in which epithelial cells are observed.

Next, urine samples were assayed in practice by adding the staining solution similar to the above-mentioned process. FIGS. 5 to 7 shows the results thus obtained. FIG. 5 is a scattergram corresponding to FIG. 2 wherein red blood cells and bacteria are observed at almost the same positions as observed in FIG. 2. On the other hand, a mass of white blood cells is observed at a somewhat upper part, compared with FIG. 2, and white blood cells having been damaged in cell membrane, etc. are scattered below. This part roughly corresponds to the white blood cells observed in FIG. 2.

FIG. 6 is a scattergram corresponding to FIG. 3 wherein epithelial cells are observed at almost the same position as observed in FIG. 3. This urine sample showed no urinary cast.

FIG. 7 is a scattergram corresponding to FIG. 4 wherein red blood cells are observed at almost the same position as observed in FIG. 4.

In each figure, Fsc stands for the forward scattered light intensity; Fl stands for the fluorescence intensity; Flw stands for the fluorescence pulse width; Fscw stands for the forward scattered light pulse width; RBC stands for red blood cells; WBC stands for white blood cells; BACT stands for bacteria; EC stands for epithelial cells; and CAST stands for blood cast.

Example 2

Assay of Standard Fluid for Urine Measurement

| <Standard fluid> | |
| --- | --- |
| HIPRESICA SP™ | 200/µl |
| Zorbax BP-SIL™ | 200/µl |
| NUCLEOPREP 100-30™ | 80/µl |

-continued

<Standard fluid>

| | |
|---|---|
| Bio-Gel A-5m(Fine)™ (particle size: 38 to 75 μm, for hyaline cast, rnanufactured by Bio-Rad Laboratories) | 13/μl |
| Pia Seed S-150™ | 200/μl |
| sodium formate | 30.5 g/l |
| hydrochloric acid | 5.0 g/l |
| ethanol (fluorescence sensitivity stabilizer) | 9.5 w/w % |
| NS-80D™ (isothiazoline-based preservative, manufactured by Nagase Kaseikogyo Co., Ltd.) | 0.01 w/w % |
| pH 4.0, conductivity: | 25 mS/cm. |

Similar to Example 1, a thick dispersion containing exclusively the particles was first prepared. After counting the particles, the dispersion was diluted and blended so as to give the above-mentioned particle concentrations.

The standard fluid was assayed under the same conditions as those employed in Example 1.

Figure 8:
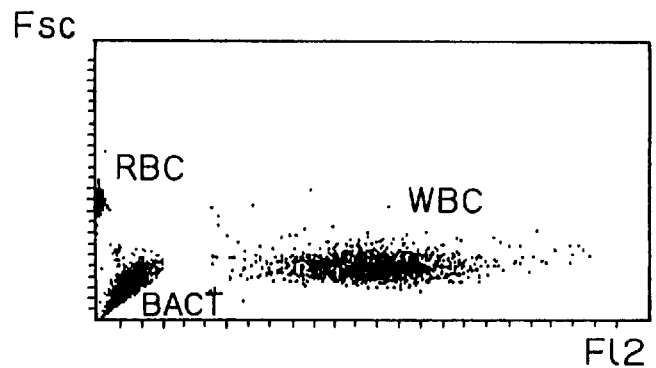
FIG. 8 is a two-dimensional scattergram of the forward scattered light intensity and the fluorescence intensity obtained by using the standard fluid containing a fluorescence sensitivity stabilizer of the present invention by which particles corresponding to red blood cells, white blood cells and bacteria can be separated and counted.

FIG. 8 is a two-dimensional scattergram of the forward scattered light intensity and the fluorescence intensity by which particles corresponding to red blood cells, white blood cells and bacteria can be separated and counted.

Figure 9:
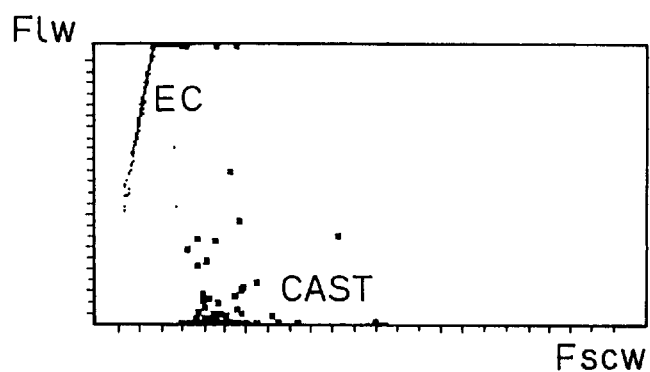
FIG. 9 is a two-dimensional scattergram of the fluorescence pulse width and the scattered light pulse width obtained by using the standard fluid containing a fluorescence sensitivity stabilizer of the present invention by which particles corresponding to epithelial cells and hyaline casts can be separated and counted.

FIG. 9 is a two-dimensional scattergram of the fluorescence pulse width and the scattered light pulse width by which particles corresponding to epithelial cells and hyaline casts can be separated and counted.

Figure 10:
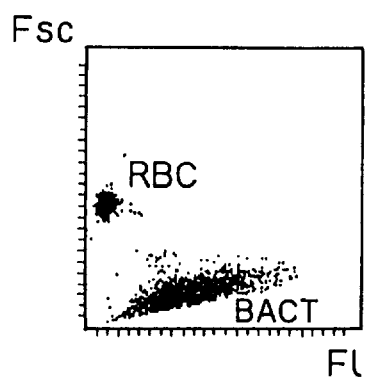
FIG. 10 is a two-dimensional scattergram of the forward scattered light intensity and the fluorescence intensity obtained by using the standard fluid containing a fluorescence sensitivity stabilizer of the present invention by which particles corresponding to red blood cells and bacteria can be separated and counted.

FIG. 10 is a two-dimensional scattergram of the forward scattered light intensity and the fluorescence intensity by which particles corresponding to red blood cells and bacteria can be separated and counted.

What is claimed is:

1. A standard fluid for calibration of a flow cytometer to be used to assay cells, said standard fluid comprising particles which adsorb stain so as to become stained when they are mixed with a staining solution to have substantially the same fluorescence intensity and scattered light intensity as those of cells to be assayed and a fluorescence sensitivity stabilizer comprising one or more water soluble organic solvents to maintain a stained mode of the particles for an extended period of time, said particles being dispersed in an aqueous medium that allows particle counting and does not materially interfere with the fluorescence and scattered light intensities of the stained particles, wherein the particles are spherical silica particles or a packing material for liquid chromatography, and wherein the cells to be assayed are selected from the group consisting of red blood cells, white blood cells, platelet, epithelial cells, urinary casts and bacteria.

2. A standard fluid for calibrating a flow cytometer as claimed in claim 1, wherein said particles are silica particles for liquid crystal spacers.

3. A standard fluid for calibrating a flow cytometer as claimed in claim 1, wherein said particles are crosslinked agarose or porous silica.

4. A standard fluid for calibrating a flow cytometer as claimed in claim 1, wherein said particles comprise two or more types of particles having fluorescence intensities and scattered light intensities different from each other.

5. A standard fluid for calibrating a flow cytometer as claimed in claim 1, wherein dye adsorption or stainability, size and surface characteristics of said particles affect particle fluorescence intensity and scattered light intensity.

* * * * *